(12) United States Patent
Dobetti et al.

(10) Patent No.: US 7,951,399 B2
(45) Date of Patent: May 31, 2011

(54) PROCESS FOR ACTIVATION OF DRUGS IN A VIBRATIONAL MILL

(75) Inventors: Luca Dobetti, Trieste (IT); Massimo Bresciani, Trieste (IT)

(73) Assignee: Eurand Pharmaceuticals Ltd., Dublin (IE)

( * ) Notice: Subject to any disclaimer, the term of this patent is extended or adjusted under 35 U.S.C. 154(b) by 360 days.

(21) Appl. No.: 10/481,378

(22) PCT Filed: Jun. 27, 2002

(86) PCT No.: PCT/EP02/07117
§ 371 (c)(1),
(2), (4) Date: Dec. 18, 2003

(87) PCT Pub. No.: WO03/002259
PCT Pub. Date: Jan. 9, 2003

(65) Prior Publication Data
US 2004/0170682 A1    Sep. 2, 2004

(30) Foreign Application Priority Data

Jun. 29, 2001 (IE) .................................... 2001/0626

(51) Int. Cl.
*A61K 9/20* (2006.01)
(52) U.S. Cl. ............. 424/465; 241/26; 241/27; 241/175
(58) Field of Classification Search .................. None
See application file for complete search history.

(56) References Cited

U.S. PATENT DOCUMENTS

| 4,932,166 | A | | 6/1990 | Boecker et al. | |
|---|---|---|---|---|---|
| 5,626,662 | A | * | 5/1997 | Urban | ........................... 106/497 |

FOREIGN PATENT DOCUMENTS

| WO | 96/32931 | | 10/1996 |
|---|---|---|---|
| WO | WO 96/32931 | * | 10/1996 |

OTHER PUBLICATIONS

Nakai et al., "Effects of Grinding on Physical and Chemical Properties of Crystalline Medicinals with Microcrystalline Cellulose. I. Some Physical Properties of Crystalline Medicinals in Ground Mixtures", *Chem. Pharm. Bull.*, 25, pp. 3340-3346 (1977).
Kawano et al., "Physichemical Properties of Ground Mixtures of Crystalline Medicinals with Microcrystalline Cellulose or Cyclodextrins," *J. Pharm. Dyn.*, 5, s-4 (1982).
Sweco Manual entitled "Installation, Operation & Maintenance Specifications for DM28L Food Grace Vibro-Energy Grinding Mill for Vectorpharma Int'l. SPA" (1997).
Nogami et al., "Studies on Powdered Preparations. XVII. Dissolution Rate of Sulfomides by Rotating Disk Method", *Chem. Pharm. Bull.*, 14, pp. 329-338 (1966).
"Pharmaceutical Technical Procedures", *European Pharmacopoeia*, pp. 141-142 (1997).

* cited by examiner

*Primary Examiner* — Robert A Wax
*Assistant Examiner* — Hasan S Ahmed
(74) *Attorney, Agent, or Firm* — Christensen O'Connor Johnson Kindness PLLC

(57) ABSTRACT

A process is described for the activation (increase in solubility and bioavailability) of drugs. The process, carried out in a vibrational mill, is characterised by the use of given proportions between the physical mixture made up of drug and pharmaceutical carrier and the empty volume among the grinding means contained inside the mill. The process leads to obtaining powders for pharmaceutical use in which the drug has a high and constant degree of activation; this result is obtainable irrespective of the nature of the drug and carrier used, and of their weight ratio.

13 Claims, 2 Drawing Sheets

PROCESS FOR ACTIVATION OF DRUGS IN A VIBRATIONAL MILL

FIELD OF INVENTION

The present invention regards the field of processes for grinding powders, in particular for pharmaceutical use. A process is described, carried out in a vibrational mill, for obtaining high and reproducible amounts of drug in a highly soluble and bioavailable form.

PRIOR ART

The formulation and administration of scarcely soluble or insoluble drugs is one of the major problems in pharmaceutical research. Frequently, such drugs show an insufficient absorption in the gastrointestinal tract and, consequently, a poor bioavailability. This leads to the production of formulations with high dosage of active principle that often must be administered several times a day to maintain a blood-plasma concentration that has therapeutic efficacy.

The factors that affect the solubility and the rate of dissolution of the molecules in water are linked to the chemical-physical properties, such as the crystalline form, the grain size, the surface area and the wettability. By adequately modifying these parameters, it is possible to improve the chemical-physical properties designed to favour the solubility of the molecules in water.

High-energy co-grinding (or mechanical-chemical activation) of crystalline drugs with inert substances (carriers), such as polymers or inorganic compounds, is a technique that enables the modification of the chemical-physical properties of the drugs and, consequently, improves their solubility in water. High-energy co-grinding enables in particular:

thermodynamic activation of the drug by means of destructuring of the crystal and formation of amorphous phase and/or nanocrystalline structures inside the carrier (Nakal et al. *Chem. Pharm. Bull.* 25, 3340, 1977; Kawano et al. *J. Pharm. Dyn.* 5, S4, 1982)

reduction in the dimensions of the particles of carrier containing the active principle, with consequent contribution to increasing the rate of dissolution of the drug itself.

The vibrational mill is an apparatus used for high-energy co-grinding. The mill is generally made up of a cylindrical chamber, or reactor, lined with inert material, inside which high-density grinding means are set. The grinding means are bodies with a defined shape, weight, volume and surface area, which are set in varying numbers inside the reactor and not fixed thereto; they are therefore free to move in response to mechanical stresses exerted, outside the reactor, by a vibratory mechanism.

To carry out grinding (and activation of the drug in the carrier), the mill is charged with a pre-set amount of grinding means and of powder to be ground, and then set in vibration. The grinding (and activation) is carried out by compression of the powder between the surfaces of the various grinding means in free roto-vibrational motion.

The vibratory mechanism is provided by an electric motor attached to the reactor, with respect to which two eccentric counterweights are positioned in an adjustable manner. The stresses exerted on the reactor cause a roto-vibrational motion of the grinding means. The transfer of energy from the motor to the grinding chamber thus depends upon the power of the motor and the weight and position of the two counterweights with respect to one another, which determine the amplitude of vibration of the chamber in the three cartesian axes. The mills are built in such a way as to allow adjustments of the weight and position of the counterweights with respect to one another (also referred to as guide angle), thereby modifying the amplitude of vibration and energy transmitted. The power of the motor is, instead, fixed and constant. (DM28L Food Grade Vibrational Mill. Sweco Manual).

The grinding means contained in the mill are generally cylindrical bodies with flat or curved (dome-shaped) bases, made of highdensity material, typically metal or metal oxide, for example, aluminium oxide, zirconium oxide or steel. The material constituting the grinding means is moreover characterised by a high consistency and resistance to impact, with the evident purpose of not releasing fragments into the powder being ground.

The capacity to activate the drug thermodynamically in the carrier and to reduce the dimensions of the particles of the carrier containing the active principle (i.e., in the final analysis to increase the rate of dissolution of the drug and its solubility) depends upon a wide range of factors. A difficulty linked to the use of vibrational mills lies in the fact that the effectiveness of grinding varies in an unforeseeable way in relation to the composition of the powder and to the quantity introduced into the mill. Therefore, it is not possible to predetermine a standard amount of filling of the mill to achieve optimal grinding, because this amount varies unforeseeably from one powder to another; for example, given the same powder/grinding means weight ratio and the same grinding conditions, results are obtained that are qualitatively very different using different drug-carrier mixtures. Therefore, for each different mixture subjected to grinding, the operator is forced to carry out numerous calibration tests, varying parameters such as the powder/grinding means ratio, until the condition for optimal activation is found. These tests are particularly burdensome not only in so far as they are lengthy and laborious, but also because operating outside the optimal conditions readily causes overheating of the mill, with consequent degradation of the active principle, damage to the grinding means, and sometimes damage to the mill itself. All this renders the application of high-energy co-grinding particularly burdensome and far from versatile.

There is therefore evident the need for a co-grinding process such as to obtain with greater ease a constant and high activation of the powders undergoing grinding. It is moreover particularly desirable to have a process that leads easily to the above results, irrespective of the chemical-physical characteristics of the powders themselves.

SUMMARY

A process is described for the activation (increased solubility and bioavailability) of drugs. The process, which is carried out in a vibrational mill, is characterised by the use of given proportions between the physical mixture made up of drug and pharmaceutical carrier and the empty volume comprised among the grinding means contained inside the mill. The process leads to obtaining powders for pharmaceutical use in which the drug has a high and constant degree of activation. This result is obtainable irrespective of the nature of the drug and carrier used, and of their weight ratio.

DETAILED DESCRIPTION OF THE INVENTION

The subject of the present invention is a process for the preparation of drug-carrier composites, performed by co-grinding a drug-carrier mixture in a vibrational mill, said process being characterised in that:

the vibrational mill contains grinding means of a cylindrical shape, with flat or convex bases, having diameter and height, independent of one another, of between 0.4 cm and 3 cm, a dimensional ratio (rd) of between 0.5 and 2, and a curvature ratio (rc) of between 0 and 0.5, a volume of drug-carrier mixture of between 35% and 100% of the empty volume comprised between the grinding means (interstitial volume VI) is used.

The vibrational mill is a known instrument, and its operating principles have been described above in the discussion of the prior art.

Figure 1:
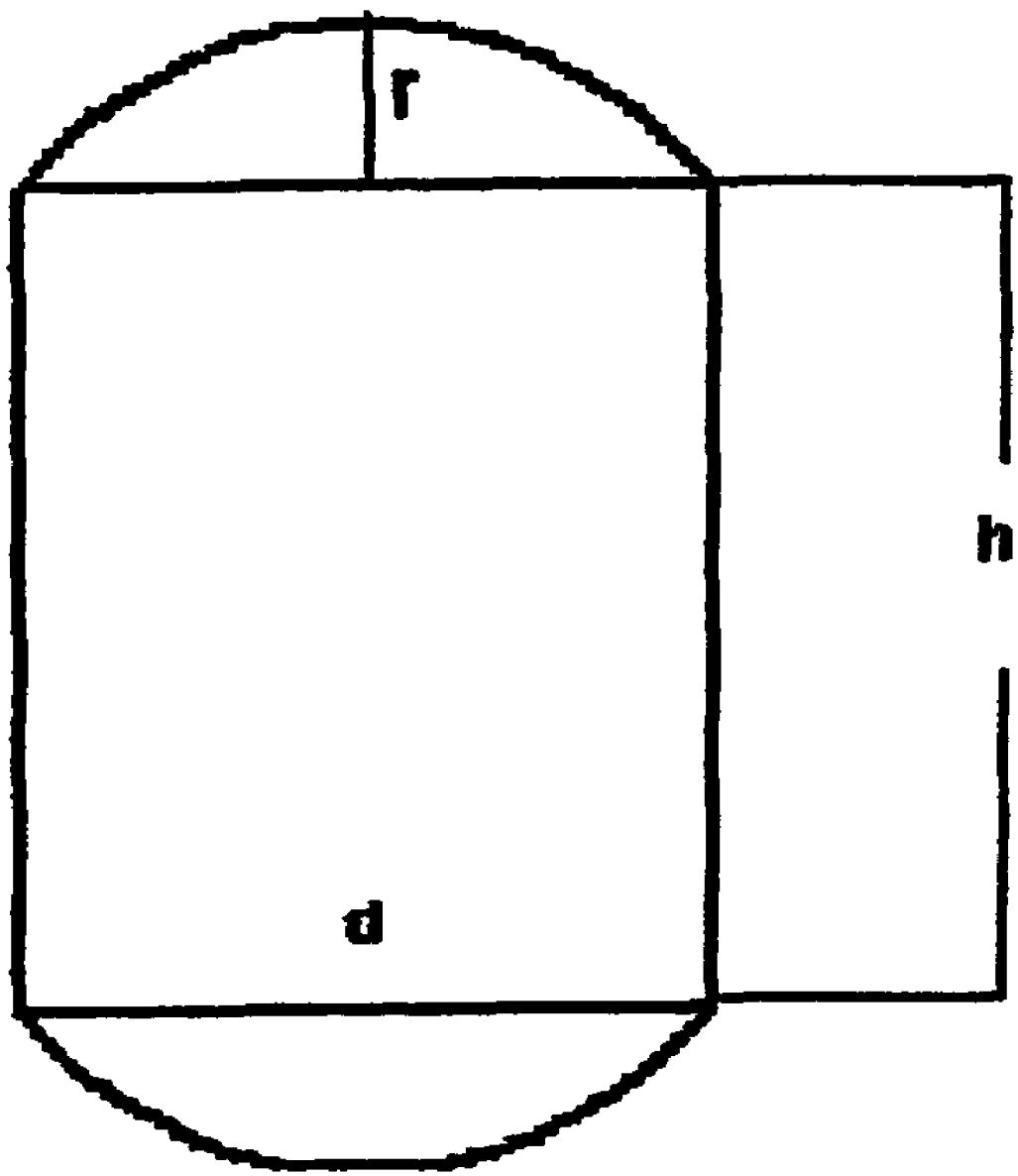
FIG. 1: Sectional view of grinding means

The dimensional ratio of the grinding means (rd) is expressed as rd=d/h, where d is the diameter and h is the height of the grinding means (see FIG. 1). The curvature ratio (rc) is expressed as rc=r/d, where r is the height of the spherical cap and d is the diameter of the grinding means (see FIG. 1). Preferred grinding means are those in which the dimensional ratio (rd) is between 0.65 and 1.5, the curvature ratio (rc) is between 0 and 0.4, and in which the diameter and height are, independently of one another, between 0.6 cm and 1.3 cm.

The grinding means are made of impact-resistant and high-density material (preferably with a density greater than 3 g/cm$^3$); examples of such materials are aluminium oxide, zirconium oxide or steel.

The grinding means are introduced into the mill in the quantities commonly used for this type of apparatus. By way of reference, the grinding means occupy from 20 to 90%, preferably from 40% to 85% of the total internal volume of the grinding chamber.

By interstitial volume ($V_i$) is meant the volume of the empty spaces comprised between all the grinding means present in the mill. The measurement of ($V_i$) is performed by introducing into the mill a liquid, for example water, and interrupting the addition of liquid when no part of the means present exceeds in height the level of the liquid, i.e., covering completely all the grinding means: the interstitial volume available is thus occupied by the liquid. The interstitial volume ($V_i$) is calculated simply by measuring the volume of used liquid or else, by measuring the difference in weight of the mill before and after the addition of the liquid and calculating the ($V_i$) via the density of the used liquid. Once it has been measured, the liquid is discharged, for example through an opening made in the base of the mill, and the residue of liquid is eliminated, for example by means of blowing in air. Next, the mill is charged with a volume of powder (mixture of drug and carrier) of between 35% and 100% of the ($V_i$) previously calculated. By "mixture" is meant simply the physical ensemble of the two powders. The effective pre-mixing of drug and carrier before introduction into the mill is altogether optional. Preferably, the drug and carrier are added in the mill as two distinct powders, taking, however, care to make sure that the sum of their volumes falls within the aforesaid range of 35-100% of ($V_i$).

The weight of powder corresponding to the volume required may be easily calculated once the density of the powder (tapped density) is known: this value may be calculated in accordance with standard procedure (see, for example. the test described by European Pharmacopoeia, 3$^{rd}$ ed., 1997, page 141).

The mill is then operated according to standard grinding conditions (as indicated in the technical manual of the equipment in use). Once grinding is completed, the activated powder is discharged from the mill and recovered.

Hence, in an operative embodiment, the process is carried out as follows:

the mill is filled with a pre-set number of the aforesaid grinding means;
the interstitial volume ($V_i$) comprised between the grinding means present in the mill is determined;
the mill is filled with a volume of mixture of drug and carrier of between 35 and 100% of $V_i$;
the mill is operated, carrying out co-grinding;
the activated drug-carrier mixture is recovered from the mill.

The drug-carrier composites obtained by the present process show a high rate of dissolution of the drug. In particular, it has been found that, operating in the drug-carrier mixture/($V_i$) volumetric ratio indicated above, stable and constant degrees of activation are obtained, irrespective of the nature of the drug-carrier mixture used. The process that forms the subject of the invention allows thus to obtain, via simple operating procedures, drug-carrier composites with high and reproducible degrees of activation.

In an advantageous variant of the process that forms the subject of the invention, once the ($V_i$) for a mill charged with the grinding means has been determined, it is possible repeat n further cycles of co-grinding in the same mill with the same grinding means on n further batches of powders (which may be composed of the same or different components), taking care to use said further batches in a volumetric amount of between 35% and 100% of the ($V_i$) as initially calculated. This variant, which is especially useful when the mill is used cyclically on an industrial scale, allows to obtain amounts of powders (even different from one another), which are highly activated and have a constant degree of activation.

The thus composite obtained may be used as such as an administrable powder for pharmaceutical uses, or may be further transformed, by means of known technologies and with the possible addition of pharmaceutical excipients, into pharmaceutical formulations suitable for administration, such as tablets, minitablets, capsules, microcapsules, granulates, pellets, suspensions, solutions, ointments, creams, implants or programmed-release devices, etc.

As far as the nature of the carrier co-ground with the drug is concerned, substantially any pharmaceutical excipient which is solid in normal conditions (for example, with a melting point, or decomposition temperature, higher than 90° C.) is usable as carrier in the present process. Non-limiting examples of carrier are cross-linked or linear polymers, such as cross-linked polyvinylpyrrolidone (PVP-CL), cross-linked carboxymethyl cellulose (croscarmellose), polacrilin potassium, starch and its derivatives such as sodium starch glycolate (SSG), cyclodextrins, cellulose and its derivatives; non-polymeric carriers such as silica or alumina are equally usable. Preferably, for the purpose of a higher activation, α-cyclodextrin, β-cyclodextrin or hydroxypropyl-β-cyclodextrin are used.

The present process may be carried out with any active principle of solid consistency under normal conditions (for example, with a melting point higher than 45° C.). The process of the invention is particularly advantageous for the drugs of low or no solubility in water, since it is on these products that the phenomenon of activation is most evident. Particularly low-solubility drugs are the ones defined as "Class II" and "Class IV" drugs according to FDA/CDER *Guidance for Industry. Waiver of in-vivo bioavailability and bioequivalence studies for immediate-release solid oral dosage forms based on a Biopharmaceutical Classification System*. August 2000. Non-limiting examples of these products are cox-2 inhibitors, antiinflammatory drugs such as nimesulide, piroxicam, naproxene, ketoprofen, ibuprofen and diacerheine, antifungal drugs such as griseofulvin, itraconazole, fluconazole, miconazole and ketonazole, bronchodilators/anti-asthmatic drugs such as zafrilukast, salbutamol, beclomethasone, flunisolide, clenbuterol, salmeterol and budesonide, steroids such as estradiol, estriol, progesterone, megestrol acetate, medroxyprogesterone acetate, antihypertensive/antithrombotict vasodilator drugs such as nefedipine, nicergoline, nicardipine, lisinopril, enalapril, nicorandil, celiprolol and verapamil, benzodiazepines such as temazepam, diazepam, lorazepam, fluidiazepam, medazepam and oxazolam, anti-migraine drugs such as zolmitriptan and sumatriptan, antilipoproteinemic drugs such as fenofibrate, lovastatin, atorvastatin, fluvastatin, and simvastatin, anti-viral/antibactetial drugs such as tosufloxacin, ciprofloxacin, ritonavir, saquinavir, nelfinavir, acyclovir and indinavir, immunodepressant drugs such as tacrolimus, rapamycine and didanisine, anti-histaminic drugs such as loratadine, antitumour drugs such as etoposide, bicalutamide, tamoxifen, doclitaxel and paclitaxel, anti-psychotic drugs such as risperidone, antiosteoporotic drugs such as raloxifene, anti-convulsant drugs such as carbamazepin and phenytoin, analgetic/narcotic drugs such as oxycodone, hydrocodone, morphine and butorpanol, muscle relaxant such as tinazadine, anti-ulcerative drugs such as famotidine. For the purposes of the present process the term "drug" comprises also the mixtures of two or more drugs.

By way of indication, the carrier and the drug are used in a weight ratio of between 12:1 and 0.5:1, preferably between 5:1 and 1:1.

The invention is now described with reference to the following non-limiting examples.

EXPERIMENTAL PART

Materials and Methods

The density of the mixtures of powders (drug and carrier) was determined in accordance with the test described in the European Pharmacopoeia, 3rd Edition (tapped density). The density was measured after carrying out 2000 beats with the prescribed instrument.

Figure 2A:
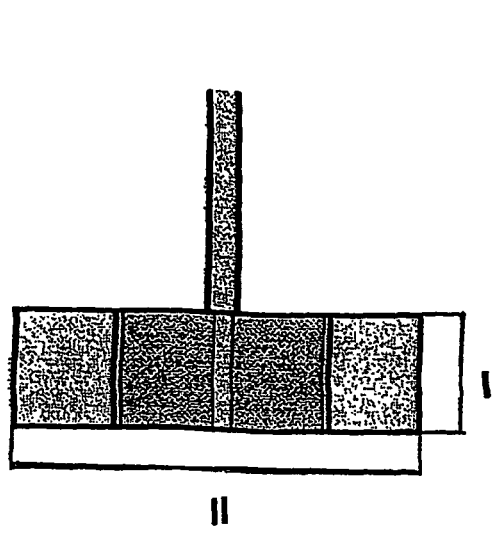
FIG. 2: Example of instrument for measuring dissolution kinetics.
  2a—Six-blade agitator (front view)
  2b—Six-blade agitator (top view)
  2c—Vessel+breakwater
Dimensions in Figures
  2a: I=2 cm; II=6 cm;
  2b: III 2 mm; IV=60°; V=6 cm
  2c: VI=16 cm; VII=1.3 cm; VIII=0.3 cm
Figure 2B:
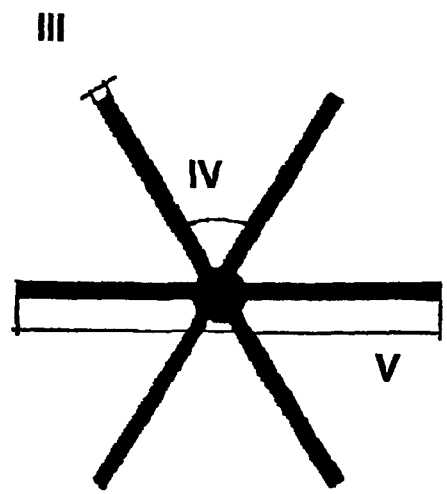
Figure 2C:
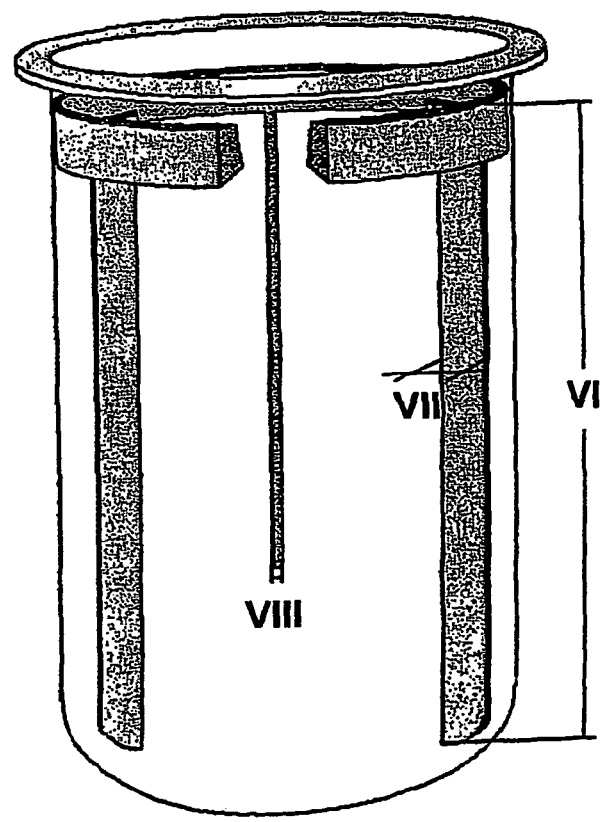

The dissolution kinetics test in conditions of supersaturation (at least 10 times higher than the solubility value of the drug) was carried out in accordance with Nogami et al. (*Chem. Pharmn. Bull.* 14, 329, 1966). The test was conducted using a six-blade turbine in a 1-L vessel in which three breakwaters were inserted. The shape and dimensions of the turbine and breakwaters are given in FIG. 2. The following operating conditions were used:

| Solvent: | Buffered aqueous solution, pH = 1.2 |
| Volume: | 500 mL |
| Temperature: | 37° C. |
| Turbine rate: | 250 rpm |
| Positioning of turbine: | 2.5 cm from bottom |
| Quantity of specimen: | equivalent to 10 times the solubility of the drug in the medium |

The solution was sampled at intervals of time and filtered. The concentration of active principle was determined by means of spectrophotometric measurement (UV-visible) or HPLC.

Example 1

Determination of the Interstitial Volume (Vi)

A determined quantity of grinding means was poured into a vibrational mill. The interstitial volume (Vi) was determined by pouring in a quantity of water until the surface level of the bed of grinding means was reached. The experimental values for the various mills used are given in Table 1.

TABLE 1

|  | Example | | |
| --- | --- | --- | --- |
|  | 1A | 1B | 1C |
| Mill | Sweco DM3 | Sweco DM28 | William-Boulton 3DM |
| Material of grinding means | Al oxide | Al oxide | Al oxide |
| Geometry of grind. means | | | |
| Diameter - d (cm) | 1.3 | 1.3 | 0.6 |
| Height - h (cm) | 1.3 | 1.3 | 0.8 |
| Dimensional ratio - rd | 1 | 1 | 0.75 |
| Curvature ratio - rc | 0 | 0 | 0.33 |
| Quantity of grinding means (kg) | 80 | 1800 | 400 |
| Interstitial volume - Vi (L) | 11 | 245 | 55 |

Example 2

In a Sweco DM28 mill, filled with grinding means according to the conditions of Example 1B, different quantities of Nimesulide and β-cyclodextrin (β-CDX) were poured in a weight ratio 1:3, according to what appears in Table 2.

The density of the physical mixture Nimesulide/β-CDX 1:3 w/w was 0.50 g/mL.

The solubility of the Nimesulide raw material was 10 μg/mL.

TABLE 2

|  | Example | | | | |
| --- | --- | --- | --- | --- | --- |
|  | 2A | 2B | 2C | 2D | 2E |
| Nimesulide (Kg) | 10 | 13 | 18 | 28 | 32 |
| β-CDX (Kg) | 30 | 39 | 54 | 84 | 96 |
| Weight of physical mixture (Kg) | 40 | 52 | 72 | 112 | 128 |
| Volume of physical mixture (L) | 80 | 104 | 144 | 224 | 256 |
| % Vri (*) | 33 | 43 | 59 | 91 | 105 |
| Kinetic Dissolution (μg/mL) | | | | | |
| Time (s): 0 |  | 0 | 0 | 0 | 0 |
| 40 |  | 19.1 | 19.0 | 19.1 | 16.1 |
| 60 | n.p. (**) | 19.9 | 19.2 | 19.8 | 16.7 |

TABLE 2-continued

| | Example | | | | |
|---|---|---|---|---|---|
| | 2A | 2B | 2C | 2D | 2E |
| 90 | | 19.6 | 19.2 | 19.6 | 16.0 |
| 150 | | 19.0 | 18.7 | 18.8 | 15.3 |
| 300 | | 18.5 | 18.4 | 18.4 | 14.8 |
| 600 | | 18.3 | 17.8 | 18.1 | 14.2 |

Std. Dev. = 1.0 µg/mL
(*) Vri = (volume (drug + carrier)/(Vi)) × 100 = % filling of the interstitial volume (Vi) by the drug + carrier mixture.
(**) n.p. = not produced: the production of the batch was not possible on account of failure of the grinding means.

As emerges from Table 2, the rate of dissolution was comparable for Examples 2B to 2D, whilst it decreased noticeably in Example 2E (Vri=105%), and was not even measurable on account of the failure to obtain of the product in the case of 2A (Vri=33%).

Example 3

In a William-Boulton 3DM mill, filled with grinding means according to the conditions of Example 1C, different quantities of Ibuprofen and sodium starch glycolate (SSG) were poured in a weight ratio 1:1, according what appears in Table 3.

The density of the physical mixture Ibuprofen/PVP-CL 1:1 w/w was 0.64 g/mL.

The solubility of the Ibuprofen raw material was 73 µg/mL.

TABLE 3

| | Example | | | | |
|---|---|---|---|---|---|
| | 3A | 3B | 3C | 3D | 3E |
| Ibuprofen (g) | 5 | 8 | 11 | 16 | 18 |
| SSG (g) | 5 | 8 | 11 | 16 | 18 |
| Weight of physical mixture (Kg) | 10 | 16 | 22 | 32 | 36 |
| Volume of physical mixture (L) | 16 | 25 | 34 | 50 | 56 |
| % Vri (*) | 29 | 45 | 62 | 91 | 102 |
| Kinetic Dissolution (µg/mL) | | | | | |
| Time (s): 0 | | 0 | 0 | 0 | 0 |
| 40 | | 135 | 142 | 144 | 99 |
| 60 | n.p. (**) | 251 | 248 | 261 | 201 |
| 90 | | 224 | 220 | 230 | 185 |
| 150 | | 200 | 201 | 205 | 163 |
| 300 | | 186 | 189 | 183 | 150 |
| 600 | | 172 | 165 | 170 | 132 |

Std. Dev. = 5 µg/mL
(*) Vri = (volume (drug + carrier)/(Vi)) × 100 = % filling of the interstitial volume (Vi) by the drug + carrier mixture.
(**) n.p. = not produced: the production of the batch was not possible on account of the increase in temperature and consequent pasting of the product due to the melting point of Ibuprofen The rate of dissolution was comparable for Examples 3B to 3D, whilst it decreased noticeably in Example 3E.

From the set of Examples 2-3 (see Tables 2-3), made with different mixtures in terms of drug, carrier and their mutual proportions, it was found that the rate of dissolution (degree of activation) of the obtained products remained high and constant within the values of Vri claimed. This shows that the application of the process that forms the subject of the invention enables to obtain powders with a high and constant degree of activation to be obtained, irrespective of the nature of the drug, of the carrier, and of the their weight ratios.

If, instead, the powder/grinding means weight ratio (w/w) had been used as reference (rather than the powder/($V_i$) volumetric ratio that forms the subject of the present invention), the interval within which activation is constant would have varied from one powder to another, as follows:
Nimesulide:β-cyclodextrin (Examples 3B-3D) 1:44-1:1:5
Ibuprofen: SSG (Examples 4B-4D) 1:35-1:12

Therefore, the use of this parameter would have required, for each powder, a series of calibration tests to determine the useful interval, a procedure that is now rendered superfluous by the present invention.

The invention claimed is:

1. A process for the preparation of drug-carrier composites, comprising co-grinding a drug-carrier mixture in a vibrational mill, wherein:
    the vibrational mill contains grinding means of a cylindrical shape, with flat or convex bases, said grinding means having: diameter and height, independently of one another, of between 0.4 cm and 3 cm, a dimensional ratio (rd) of between 0.5 and 2, and a curvature ratio (rc) of between 0 and 0.5; and
    the vibrational mill is charged with a volume of drug-carrier mixture of between 35% and 100% of the interstitial volume $V_i$, wherein interstitial volume $V_i$ is the volume of empty spaces between the grinding means in the mill.

2. The process according to claim 1, where the grinding means have a diameter and height, independently of one another, of between 0.6 cm and 1.3 cm, a dimensional ratio (rd) of between 0.65 and 1.5, and a curvature ratio (rc) of between 0 and 0.4.

3. The process according to claim 1, wherein the grinding means occupy from 20% to 90% of the total internal volume of the grinding chamber.

4. The process according to claim 1, where the grinding means comprise aluminum oxide, zirconium oxide or steel.

5. The process according to claim 1, where the carrier is a solid substance for pharmaceutical use selected from the group consisting of cross-linked polymers, linear polymers, and non-polymeric carriers.

6. The process according to claim 1, where the carrier and the drug are used in a weight ratio of between 12:1 and 0.5:1.

7. The process according to claim 1, where the composite obtained by co-grinding is further transformed, with the optional addition of pharmaceutically acceptable excipients, into pharmaceutical formulations suitable for human or animal administration.

8. The process according to claim 7, where said pharmaceutical formulations are selected from the group consisting of tablets, minitablets, capsules, microcapsules, granulates, pellets, suspensions, solutions, ointments, creams, implants and programmed-release devices.

9. A process for the preparation of a given number (n) of drug-carrier batches with a constant degree of activation, comprising n cycles of co-grinding drug-carrier mixtures, each having the same composition, in the same vibrational mill containing the same grinding means, wherein:
    the vibrational mill contains grinding means of a cylindrical shape, with flat or convex bases, having: diameter and height, independently of one another, of between 0.4 cm and 3 cm, a dimensional ratio (rd) of between 0.5 and 2, and a curvature ratio (rc) of between 0 and 0.5; and
    the vibrational mill is charged with a volume of drug-carrier mixture of between 35% and 100% of the interstitial volume $V_i$, wherein the interstitial volume $V_i$ is the volume of empty spaces between the grinding means in the mill and in which the interstitial volume $V_i$ is determined only once and is used as a reference for all the n grinding cycles, wherein the n cycles of co-grinding with the vibrational mill so charged produce n drug-carrier batches with a constant degree of activation.

10. A process for the preparation of drug-carrier composites, performed by co-grinding a drug-carrier mixture in a vibrational mill, wherein:

the vibrational mill contains grinding means of a cylindrical shape, with flat or convex bases; and the vibrational mill is charged with a volume of drug-carrier mixture of between 35% and 100% of the interstitial volume $V_i$, wherein the interstitial volume $V_i$ is the between the grinding means in the mill.

11. The process of claim 10, wherein the grinding means have: diameter and height, independently of one another, of between 0.4 cm and 3 cm, a dimensional ratio (rd) of between 0.5 and 2.

12. The process of claim 11, wherein the grinding means have a curvature ratio (rc) of between 0.1 and 0.5.

13. The process according to claim 10, where the grinding means have a diameter and height, independently of one another, of between 0.6 cm and 1.3 cm, a dimensional ratio (rd) of between 0.65 and 1.5, and a curvature ratio (rc) of between 0.1 and 0.4.

* * * * *

UNITED STATES PATENT AND TRADEMARK OFFICE
CERTIFICATE OF CORRECTION

PATENT NO. : 7,951,399 B2  
APPLICATION NO. : 10/481378  
DATED : May 31, 2011  
INVENTOR(S) : L. Dobetti et al.

Page 1 of 1

It is certified that error appears in the above-identified patent and that said Letters Patent is hereby corrected as shown below:

| COLUMN | LINE | ERROR |
|---|---|---|
| 9 | 12 | Before "between the grinding means" insert --volume of empty spaces-- |

Signed and Sealed this  
Fourth Day of October, 2011

David J. Kappos  
*Director of the United States Patent and Trademark Office*